United States Patent [19]
O'Brien et al.

[11] Patent Number: 5,556,557
[45] Date of Patent: Sep. 17, 1996

[54] METHOD OF PARTITIONING BLOOD USING POLYESTERS

[75] Inventors: William L. O'Brien, Cincinnati; Alan C. Kilbarger, Milford, both of Ohio

[73] Assignee: Henkel Corporation, Plymouth Meeting, Pa.

[21] Appl. No.: 463,374

[22] Filed: Jun. 5, 1995

Related U.S. Application Data

[62] Division of Ser. No. 390,898, Feb. 16, 1995, Pat. No. 5,506,333, which is a continuation of Ser. No. 100,535, Jul. 30, 1993, abandoned.

[51] Int. Cl.⁶ .................... B01D 21/26; C08G 63/02
[52] U.S. Cl. .................. 210/787; 210/516; 210/518; 210/789; 252/1; 252/60; 528/272
[58] Field of Search ................... 210/782, 789, 210/516, 518, 787; 528/272, 295.3, 296, 300, 302, 303, 307, 308.6; 525/165, 168, 174; 252/60, 1

[56] References Cited

U.S. PATENT DOCUMENTS

| | | | |
|---|---|---|---|
| 4,101,422 | 7/1978 | Lamont et al. | 210/516 |
| 4,148,764 | 4/1979 | Lamont et al. | 210/516 |
| 4,172,803 | 10/1979 | Ichikawa et al. | 252/60 |
| 5,101,009 | 3/1992 | Nakane et al. | 528/272 |
| 5,124,434 | 6/1992 | O'Brien | 528/272 |
| 5,176,956 | 1/1993 | Jevne et al. | 428/375 |

*Primary Examiner*—John Kim
*Attorney, Agent, or Firm*—Wayne C. Jaeschke; John E. Drach; Henry E. Millson, Jr.

[57] ABSTRACT

A polyester is provided which facilitates the separation of blood into light and heavy phases via centrifugation in a blood collection vessel. The polyester is useful as a component of a partitioning composition formulated to have appropriate specific gravity to be positioned intermediate the light and heavy blood phases during centrifugation. A partitioning composition including a polyester of the invention provides a particular advantage in blood collection vessels due to its lighter and more consistent coloration. The polyester composition can be prepared with relative ease compared to prior art polyesters useful in blood partitioning compositions.

14 Claims, No Drawings

METHOD OF PARTITIONING BLOOD USING POLYESTERS

This application is a divisional application of Ser. No. 08/390,898, filed on Feb. 16, 1995, now U.S. Pat. No. 5,506,333, which is a continuation of application Ser. No. 08/100,535, filed on Jul. 30, 1993, now abandoned.

BACKGROUND OF THE INVENTION

1. Field of the Invention

The present invention relates to polyesters useful for facilitating the separation of blood serum or plasma from the cellular portion of blood.

2. Description of the Related Art

The polyesters of the invention are conveniently formulated into a partitioning composition for use in a blood collection vessel in which the blood sample is subjected to centrifugation until the cellular portion and serum or plasma are completely separated. The physical and chemical properties of the partitioning compositions are such that a continuous, integral seal is provided between the separated blood phases, thereby maintaining separation of the phases after centrifugation and simplifying removal of the serum or plasma from the blood collection vessel. The high volume testing of blood components in hospitals and clinics has led to the development of various devices to simplify the collection of blood samples and preparation of the samples for analysis. Typically, whole blood is collected in an evacuated, elongated glass tube that is permanently closed at one end and sealed at the other end by a rubber stopper having a diaphragm which is penetrated by the double-tipped cannula used to draw the patient's blood. After the desired quantity of blood is collected, the collection vessel is subjected to centrifugation to yield two distinct phases comprising the cellular portion of the blood (heavy phase) and the blood serum or plasma (light phase). The light phase is typically removed from the collection vessel, e.g., via pipette or decantation, for testing.

It has been proposed heretofore to provide manufactured, seal-forming members, e.g., resilient pistons, spools, discs and the like, in blood collection vessels to serve as mechanical barriers between the two separated phases. Because of the high cost of manufacturing such devices to the close tolerances required to provide a functional seal, they have been supplanted by fluid sealant compositions. Fluid sealant compositions are formulated to have a specific gravity intermediate the two blood phases sought to be separated, so as to provide a partition at the interface between the cellular and serum phases. Such compositions typically include a polymer base material, one or more additives for adjusting the specific gravity and viscosity of the resultant composition, and optionally, a network former. Representative prior art fluid sealant compositions include: styrene beads coated with an anti-coagulant (U.S. Pat. No. 3,464,890); silicone fluid having silica dispersed therein (U.S. Pat. No. 3,780,935); a hydrophobic copolyester including a suitable filler, e.g., silica (U.S. Pat. Nos. 4,101,422 and 4,148,764); a liquid alpha-olefindialkylmaleate, together with an aliphatic amine derivative of smectite clay or powdered silica (U.S. Pat. No. 4,310,430); the reaction product of a silicone fluid with a silica filler and a network former (U.S. Pat. No. 4,386,003); a mixture of compatible viscous liquids, e.g., epoxidized vegetable oil and chlorinated polybutene, and a thixotropy-imparting agent, e.g., powdered silica (U.S. Pat. No. 4,534,798); a thixotropic gel comprising a dual resin component including poly-alpha-pinene of lower density combined with chlorinated octadecene of higher density, said gel further comprising a radiation stabilizer, a network stabilizer, a thixotropic agent and a pigment (U.S. Pat. No. 4,994,393); and a gelatinous material admixed with fine resin particles having an average particle size of 0.01 to 2 microns and having an internal crosslinking density of 0.1 to 3 mmol/g (U.S. Pat. No. 5,169,543).

Ideally, a commercially useful blood partitioning composition should maintain uniform physical and chemical properties for extended time periods prior to use, as well as during transportation and processing of blood samples, readily form a stable partition under normal centrifugation conditions and be relatively inert or unreactive toward the substance(s) in the blood whose presence or concentration is to be determined. Inertness to substances sought to be determined is a particular concern when blood collection vessels are used for therapeutic drug monitoring (TDM), which is assuming an increasingly important role. TDM is established through the accumulated experience of clinicians, and consequently reduces the number of patients receiving dosage levels that are either below detection limits or toxic. Administration of drugs under TDM allows one to take into account such factors as drug tolerance developed with passage of time, presence of multiple physical disorders and synergistic or antagonistic interactions with other therapeutic agents. Among the drugs recommended for administration under TDM are those having dangerous toxicity with poorly defined clinical endpoint, steep dose-response curve, narrow therapeutic range considerable inter-individual pharmacokinetics variability or nonlinear pharmacokinetics, as well as those used in long term therapy or in the treatment of life-threatening diseases. By way of example, the evaluation of blood levels of a number of tricyclic antidepressant compounds, such as imipramine or desipramine, in relation to an empirically established therapeutic range is reported to be particularly useful in the treatment of seemingly drug-refractive depression. TDM is likewise used to monitor the dosage of anficonvulsant drugs, such as phenytoin and phenobarbital which are administered in the treatment of epilepsy, antitumor drugs, such as methotrexate, and other more commonly prescribed drugs, including, but not limited to digoxin, lidocaine, pentobarbital and theophylline.

Reports of recent studies on the effect of blood partitioning compositions on drug concentrations in serum and plasma indicate that care must be taken in the selection of polymeric materials which come into contact with the blood samples obtained for drug assay. See, for example, P. Orsulak et al., Therapeutic Drug Monitoring, 6:444–48 (1984) and Y. Bergqvist et al. Clin. Chem., 3:465–66 (1984). The results of these studies show that the blood partitioning compositions provided in blood collection vessels may account for reduced serum or plasma values, as a result of drug absorption by one or more components of the composition. The reported decreases in measured drug concentrations appears to be time-dependent. One report concludes that the observed decreases in drug concentrations may effectively be reduced by minimizing the interval between collection and processing. Another report recommends that blood samples be transported to the laboratory as soon as possible, with processing occurring within 4 hours. A commercially useful blood collection vessel, however, must produce accurate test results, taking into account routine clinical practices in large institutions, where collection, transportation and processing of blood samples may realistically take anywhere from about 1–72 hours.

U.S. Pat. No. 4,148,764 teaches polyesters useful as a barrier material in blood separation assemblies. The polyesters are comprised of the reaction products of essentially stoichiometric quantities of: (1) a dicarboxylic acid component which is comprised of: (a) aliphatic dicarboxylic acid having from 4 to about 12 carbon atoms, (b) a polymeric fatty acid containing 75% by weight or more of a C36 dibasic acid; (2) a diol component which includes a branched-chain aliphatic dihydric alcohol having 3 to 8 carbon atoms, a mixture of these dihydric alcohols, or a mixture containing at least 50% by weight of the branched-chain aliphatic dihydric alcohols and a straight-chain aliphatic dihydric alcohol having 2 to 8 carbon atoms. The equivalents ratio of (a) to (b) ranges from 0.80:0.20 to 0.97:0.03. The polyesters have an average molecular weight of 2,000–10,000, a kinematic viscosity at 210° F. of 2,000–8,000 centistokes, and a density in the range of from 1.015 to 1.060 g/cm$^3$ at 25° C.

U.S. Pat. No. 5,124,434 discloses polyesters useful in blood partitioning wherein the polyesters comprise at least four components, namely about one mole of a dicarboxylic acid member and one mole of a diol member wherein said acid member is comprised of a first dicarboxylic acid component having from about 5 to about 60 mole percent of an aliphatic dicarboxylic acid having from 13 to about 22 carbon atoms, a second dicarboxylic acid component having from about 35 to about 90 mole percent of an aliphatic dicarboxylic acid having from 4 to about 12 carbon atoms, and a third dicarboxylic acid component having from about 5 to about 25 mole percent of an aliphatic dicarboxylic acid having about 36 carbon atoms, said polyester being in the form of a viscous liquid and having a density at room temperature in the range of 1.01–1.09. However, U.S. '434 does not suggest the use of dimer diol, a 36 carbon atom dihydric alcohol, as a useful diol member. Also, there is no teaching that a polyester useful in functional blood partitioning compositions having reduced affinity for therapeutic agents present in blood such as phenobarbital and imipramine can be prepared from only three ingredients. The ability to make fluid hydrophobic polyesters with precise density control from three rather than four ingredients provides obvious advantages in terms of simplifying the manufacturing process for their preparation. Fewer reactants means there are fewer opportunities for making errors in charging the reactants to the reaction vessel. Production efficiency is also improved due to the relatively high rate of polycondensation observed during the preparation of the polyesters of the instant invention. It has been observed that the dimer diol containing polyesters are lighter in color than the dimer acid containing polyesters taught in U.S. Pat. No. 5,124,434. The dimer diol apparently affords reduced susceptibility to thermal-oxidative darkening under the reaction conditions employed to prepare polyesters. In addition, when looking at batch to batch variability, the use of dimer diol generates polyesters which have a more nearly constant color than exhibited by the dimer acid containing polyesters. The lighter, and more consistent color of the dimer diol polyesters facilitates color matching when those polyesters are employed in silica-polyester-stabilizer functional blood partitioning compositions.

British patent 685,649 discloses a process for the preparation of polyesters made by reacting succinic acid having an open chain hydrocarbon radical containing from 18 to 26 carbon atoms directly joined to at least one of the methylene groups and an organic compound having two esterifiable hydroxyl groups.

U.S. Pat. No. 4,480,087 teaches polyester waxes which contain as the acid member at least 75 mole percent of alkylsuccinic anhydride or alkenylsuccinic anhydride and the acid functional derivatives thereof, and linear aliphatic and cycloaliphatic glycols having from 2 to 12 carbon atoms as the diol member. The remaining acid member may be a $C_4$ to $C_{10}$ dibasic aliphatic acid such as succinic or adipic acid. The patent does not teach polyester compositions incorporating a 36 carbon atom diol member, nor does it contain any suggestion that such polyester compositions are useful as functional blood partitioning compositions having reduced affinity for therapeutic agents present in blood such as phenobarbital and imipramine.

U.S. Pat. No. 5,101,009 relates to copolyester resins which contain as the acid member either terephthalic acid or a dialkyl terephthalate, and contain as the diol member both a dimer diol and at least one glycol having 2 to 8 carbon atoms. The patent does not teach the use of aliphatic diacids as the acid member, nor does it contain any suggestion that such copolyester compositions are useful as functional blood partitioning compositions having reduced affinity for therapeutic agents present in blood such as phenobarbital and imipramine.

U.S. Pat. No. 5,176,956 discloses an improved biomedical appliance having disposed on a skin-contacting, operant portion thereof, a film or layer of a skin compatible, tacky, pressure sensitive polymeric adhesive, the reaction product consisting of at least on fatty acid dimer based or derived component, including dimer diol, and a suitable co-reactant, including dihydric alcohols. The patent does not contain any suggestion that their polyester compositions are useful as functional blood partitioning compositions having reduced affinity for therapeutic agents present in blood such as phenobarbital and imipramine.

SUMMARY OF THE INVENTION

In accordance with the present invention, it has been discovered that certain highly hydrophobic polyesters satisfy the above-noted criteria for incorporation in a clinically useful blood partitioning composition. The polyesters according to the invention comprise a dicarboxylic acid member and a diol member.

The diol member is comprised of dimer diol, a 36 carbon atom dihydric alcohol available from the hydrogenation of dimer acid, where dimer acid is produced by the dimerization of 18 carbon atom fatty acids. The polyester is in the form of a viscous liquid having a density at room temperature in the range of about 1.01 to about 1.09.

More particularly, the polyesters of the invention comprise as repeating units:

A= (—O—$R_A$—O—) and
B=

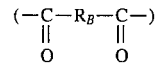

wherein $R_A$ has 36 carbon atoms of the empirical formula:

and $R_B$ is a member selected from the group consisting of a divalent aliphatic chain of 1–34 carbon atoms, a divalent cycloaliphatic chain of 3–34 carbon atoms, a divalent arylene chain of from 9–34 carbon atoms, a divalent alkarylene chain of from 7–34 carbon atoms, and a divalent alkarylene chain of from 8–34 carbon atoms and mixtures thereof. Alternatively, the polyester may comprise the following repeating units.

$A = (-O-R_A-O-)$ $B =$

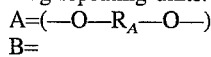

and $C = (-O-R_C-O-)$ wherein $R_A$ and $R_B$ are as defined above.

and $R_C$ is a member selected from the group consisting of compounds of the formula:

$R_C = (CH_n R_m)_k$ where n=0, 1, 2, or 3

R=H, $C_1$ to $C_{10}$ alkyl m=0, 1, or 2 n+m=2 k=1 to 10

These include for example, 1,2 propylene glycol, 1,3 and 1,4 butanediol, 3-methyl 1,5 penanediol and the like.

The incorporation of the $C_{36}$ dihydric aliphatic alcohol into the polyesters of the present invention produces a product which, when formulated together with other ingredients such as suitable filler and compatible surfactant, is a functional blood partitioning composition.

The polyesters of the invention are readily formulated together with other ingredients, typically a suitable filler and compatible surfactant, into functional blood partitioning compositions. The density of the finished blood partitioning composition is controlled within prescribed limits, so that during centrifugation the composition becomes stably positioned at the interface between the serum or plasma phase and heavier cellular phase and, when centrifugation is terminated, forms a continuous integral barrier within the blood collection vessel to prevent the two phases from recombining or mixing, especially when decanting or pipetting the serum or plasma. The blood partitioning compositions of the invention are advantageously employed in small amount, on the order in a 10 ml blood collection vessel of the type previously described which are then ready for use in blood sampling and analysis in the usual way. The polyester-based blood partitioning compositions of the invention are especially suited for use in TDM procedures, displaying negligible interaction with commonly monitored therapeutic agents.

DESCRIPTION OF THE PREFERRED EMBODIMENTS

The polyesters according to the invention having the repeating units as set forth above, have molecular weights from about 3,000 to about 12,000 (number average, as determined by gel permeation chromatography). The polyesters of the invention are produced in the form of viscous liquids, having a density at room temperature in the range of 1.01 to 1.09. Particularly notable among the properties of these polyesters is their light color and the batch to batch consistency of the polyester coloration. Also notable among the properties of these polyesters is their inertness, making them especially useful in TDM programs. The polyesters of the invention are also highly hydrophobic, exhibiting negligible water solubility. The physical and chemical properties of these polyesters are uniformly maintained over extended periods prior to use, as well as during transportation and processing of blood samples. Among the other notable characteristics of these polyesters is the ability to undergo ultracentrifugation for up to 1 hour at up to 1500G (G being the ratio of centrifugal acceleration to acceleration of gravity), without any detectable adverse effect.

The polyesters of the invention are further characterized by having an acid value of 2 or less, an hydroxyl value of 25 or less and a 210° F. kinematic viscosity of about 1700–5000 centistokes.

Polyesters having the above-described properties are especially useful as blood partitioning agents in blood collection vessels where they provide a continuous integral barrier or seal between the serum and clot portions of blood. In other words, the polyester completely partitions the separated phases so that the serum and cellular or clot portions are no longer in contact at any point, forming a unitary seal which firmly adheres to the inner surface of the blood collection vessel. By forming a continuous, integral barrier in this way, it is possible to easily remove the serum or plasma portion by decanting or pipetting, with the clot portion remaining undisturbed in the collection vessel.

As described above, the polyesters of this invention comprise a dicarboxylic acid member and a diol member. Diacids suitable for use as the dicarboxylic acid member include dicarboxylic acids of the formula:

$HOOC-R_1-COOH$ where $R_1$ is a divalent alkylene chain having from 1 to 46 carbon atoms, and preferably is selected from the group consisting of divalent aliphatic chains of 1–34 carbon atoms, divalent cycloaliphatic chains of 3–34 carbon atoms, arylene chains of from 6–34 carbon atoms, alkarylene chains of from 7–34 carbon atoms, and alkarylalkylene chains of from 8–34 carbon atoms.

Suitable diacids useful in the practice of the present invention include, but are not limited to oxalic acid, malonic acid, succinic acid, methylmalonic acid, fumaric acid, maleic acid, acetylene dicarboxylic acid, glutaric acid, ethylmalonic acid, dimethylmalonic acid, methylsuccinic acid, citraconic acid, glutasconic acid, itaconic acid, mesaconic acid, adipic acid, 2-dimethylsuccinic acid, 3-methylglutaric acid, hydromuconic acid, muconic acid, pimelic acid, butylmalonic acid, diethylmalonic acid, 2-dimethylglutaric acid, 2-ethyl, 2-methylsuccinic acid, 3-methyladipic acid, cyclopentanedicarboxylic acid, suberic acid, cyclohexanedicarboxylic acid, isophthalic acid, terephthalic acid, azelaic acid, 5-norbornene-2,3-dicarboxylic acid, phenylmalonic acid, sebacic acid, camphoric acid, 1-cyclohexanediacetic acid, cyclohexylsuccinic acid, benzylmalonic acid, phenylene diacetic acid, phenylsuccinic acid, undecanedioic acid, 3-phenylglutaric acid, 1.10-decanedicarboxylic acid, 4-phenylenedipropionic acid, naphthalene dicarboxylic acid, 1.11-undecanedicarboxylic acid, 1.12-dodecanedicarboxylic acid, 4-biphenyldicarboxylic acid, diphenic acid, hexadecanedioic acid, dimer acids and mixtures thereof. Especially preferred are adipic, azelaic, sebacic, and dodecanedioic acids.

It will be apparent to those skilled in the art that the various art-recognized equivalents of the aforementioned dicarboxylic acids, including lower alkylesters and anhydrides and lower alkyl esters thereof, may be employed in preparing the polyesters of the invention. Accordingly, as used herein, the term "acid" is intended to encompass such acid derivatives. Methyl esters are particularly advantageous for the preparation of the polyesters described herein. Mixtures of acids, anhydrides and esters may also be reacted to obtain the desired product.

The diol member of the polyesters of the invention comprises a dimer diol, component having as a main component a compound of the formula $R_A$ as defined above.

These dimer diols are more fully described in U.S. Pat. No. 5,101,009 which is incorporated herein by reference.

The diol member may additionally comprise one or more esterifiable dihydric compounds of the formula:

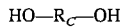
$$HO{-}R_C{-}OH$$

Representative diols falling within the foregoing formula include neopentyl glycol, propylene glycol, diethylene glycol, triethylene glycol, 3-methyl- 1,5-pentane diol, 1,2 propane diol, 1,3-butane diol, 1,2-butane diol, 1,2-pentane diol, 1,3-pentane diol, 1,4-pentane diol and the like. The diol member comprises dimer diol and propylene glycol where the molar ratio of dimer diol to propylene glycol charged to the reaction vessel ranges from about 0.17:0.99 to about 0.42:0.78.

Conventional esterification procedures and equipment are used to obtain the polyester of the invention. The reactive components are normally added to the reaction vessel as a unit charge and the reaction mixture is then heated with agitation at a temperature from about 150°–250° C. for a period of time sufficient to substantially complete the esterification reaction. The reaction may be driven to completion by application of vacuum (typically 1–5 mm Hg absolute at 200°–250° C.) until the desired properties are obtained. Vacuum distillation removes the final traces of water, any excess reactants and small amounts of other volatile materials present in the reaction mixture.

While the polyesters of the invention are formed with notably light coloration, if a further improvement in color is desired, the polyester may be bleached by any of the well known and accepted bleaching methods, e.g., using hydrogen peroxide or chlorite. Alternatively, the polyester may be decolorized by filtering through a filter aid, e.g., charcoal or bleaching clay.

The rate of esterification may be enhanced by the use of known esterification catalysts. Suitable esterification catalysts for enhancing the rate of esterification of free carboxyl groups include phosphoric acid, sulfuric acid, toluenesulfonic acid, methane sulfonic acid, and the like. The amount of such catalyst may vary widely, but most often will be in an amount from about 0.1% to about 0.5% by weight, based on the total reactant charge. Catalysts useful for effecting ester interchange include dibutyltin diacetate, stannous oxalate, dibutyltin oxide, tetrabutyl titanate, zinc acetate and the like. These catalysts are generally employed in an amount ranging from about 0.01% to 0.05% by weight, based on the total resistant charge. When such catalysts are used, it is not necessary that they be present throughout the entire reaction. It is sometimes advantageous in order to obtain products having good color and relatively low acid value, on the order of 2 mg KOH/gm, or less, to add the catalyst during the final stages of the reaction. Upon completion of the reaction, the catalyst may be deactivated and removed by filtration or other conventional means.

Inert diluents, such as benzene, toluene, xylene and the like may be employed for the reaction. However, the use of diluents is not necessary. It is generally considered desirable to conduct the reaction without diluents since the resultant polyester can be directly used as it is obtained from the reaction vessel. A small excess (based on the equivalents of acid present) of a volatile diol component may be used if desired. The excess diol serves as the reaction medium and reduces the viscosity of the reaction mixture. The excess diol is distilled off as the esterification is carried to completion and may be recycled to the reactor if desired. Generally, about 20% by weight excess volatile diol will suffice.

A particularly useful blood partitioning agent is obtained by reacting a total of 1.0 mole of acid member which comprises adipic acid, with about 1.2 moles of a diol member comprising dimer diol and propylene glycol. The molar ratio of dimer diol to propylene glycol ranges from about 0.17:0.99 to about 0.42:0.78.

Preparation of blood partitioning compositions using the polyesters of the invention may be carried out in the manner described in commonly owned U.S. Pat. Nos. 4,101,422 and 4,148,764, the entire disclosures of which are incorporated by reference in the present specification, as if set forth herein in full.

Determination of the extent of interaction between the polyesters of the invention and commonly monitored drugs may be carried out using well known recovery experiments and drug measurement techniques, such as, gas chromatography, gas-liquid chromatography, high-performance liquid chromatography, thin layer chromatography or immunoassay techniques, including radioimmunoassay, enzyme immunoassay, fluorescence polarization immunoassay, nephelometric assay, and the like. A variety of suitable procedures are reported in the literature. See, for example Bergqvist et at., supra. Such determinations may be carried out using human serum, or commercially available bovine serum, if desired.

The following examples are presented to illustrate the invention more fully, and are not intended, nor are they to be construed, as a limitation of the scope of the invention. In the examples, all percentages are on a weight basis unless otherwise indicated.

EXAMPLE 1

1.30 kilograms of a reaction mixture comprising adipic acid (Equivalent fraction 1.0, 41.91 wt. %), 1,2-propyleneglycol (Equivalent fraction 0.75+20% excess, 19.63 wt. %), and dimerdiol (Equivalent ratio 0.25, 38.46 wt. %, no excess used) was added in a 2-liter reaction flask equipped with a mechanical stirring device, an electronic thermostat, and an insulated Vigreaux fractioning column leading into a recycle trap mounted underneath a reflux condenser, and heated gradually to a final temperature of about 225° C. The onset of esterification was observed as the temperature reached about 190° when water began to accumulate in the trap. The heating rate was adjusted to maintain the temperature of the condensing vapors in the range 100°–110°, allowing the action of the fractionating column to return volatile glycol to the reaction vessel with maximum efficiency. After about 8 hours, when about 85% of the theoretical water of reaction had been collected, the apparatus was evacuated, lowering the internal pressure by 28 inches of Hg. With this degree of evacuation and a reactor temperature of 225°, the conversion of acid groups to esters was essentially complete in 1.5 hours (total elapsed time, 9.5 hours). A transesterification catalyst, namely di-n-butyltin diacetate, was then introduced at a concentration equal to 0.02% of the initial charge. The fractionating column was isolated from the system in favor of a shortened distillation path, and the apparatus was evacuated to the maximum capacity of a "rough" laboratory pump (1–2 mmHg). In about 0.75 hours, the viscosity rose to 3477 cSt @210° F. The finished product had an acid value of 0.4 mg KOH/g. and a hydroxyl value of 20.7 (same units). Density of the polyester was 1.0266 gm./mL at 25° C.

While the present invention has been described and exemplified above in terms of certain preferred embodiments, various other embodiments may be apparent to those skilled in the art. Accordingly, the invention is not limited to the embodiments specifically described and exemplified, but variations and modifications may be made therein and thereto without departing from the spirit of the invention, the full scope of which is delineated by the following claims.

What is claimed is:

1. A method of partitioning blood comprising the steps of:
   (i) placing an effective amount of a polyester comprising the repeating units A and B of the formula:
   A=the group ($-O-R_A-O-$) from a dimer diol and
   B=

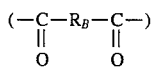

wherein $R_A$ has the empirical formula:

$C_{36}H_{70}$ and $R_B$ is a member selected from the group consisting of a divalent aliphatic chain of 1–34 carbon atoms, a divalent cycloaliphatic chain of 3–34 carbon atoms, a divalent arylene chain of from 9–34 carbon atoms, a divalent alkylene chain of from 7–34 carbon atoms, and a divalent alkaryalkylene chain of from 8–34 carbon atoms, and mixtures thereof, in combination with a filler and a compatible stabilizer, and optionally a pigment into a blood collecting tube,
   (ii) introducing the blood to be partitioned, and
   (iii) effecting the partitioning of the said blood through the action of centrifugal force.

2. The method of claim 1 wherein $R_B$ is a member selected from the group consisting of a divalent aliphatic chain of 3–34 carbon atoms, and said polyester exhibits a room temperature density in the range of about 1.01–1.09, a kinematic viscosity of about 1700 centistokes to 5000 centistokes at 210° F., an hydroxyl value of 25 or less, and an acid value equal to 2 or less.

3. The method of claim 1 wherein said polyester comprises the repeating units A, B, and C of the formula:
   A=the group ($-O-R_A-O-$) from a dimer diol
   B=

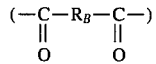

and
   C=($-O-R_C-O-$)

wherein $R_A$ has the empirical formula:

$C_{36}H_{70}$ and $R_B$ is a member selected from the group consisting of a divalent aliphatic chain of 1–34 carbon atoms, a divalent cycloaliphatic chain of 3–34 carbon atoms, a divalent arylene chain of from 9–34 carbon atoms, a divalent alkylene chain of from 7–34 carbon atoms, and a divalent alkaryalkylene chain of from 8–34 carbon atoms, and mixtures thereof,
   and $R_C$ is a member selected from the group consisting of compounds of the formula:

$R_C=(CH_nR_m)_k$ where
   n=0, 1, 2, or 3
   R= H or a $C_1$ to $C_{10}$ alkyl
   m=0, 1, or 2
   n+m=2
   k=1 to 10.

4. The method of claim 3 wherein $R_B$ is a divalent aliphatic chain containing 3 to 34 carbon atoms.

5. The method of claim 3 wherein the polyester has a hydroxyl value of less than 25 and an acid value of 2 or less.

6. The method of claim 3 wherein in the polyester $R_B$ is $-(CH_2)_2-$ and $R_C$ is $-CH(CH_3)-CH_2-$.

7. The method of claim 6 wherein the molar ratio of $R_B$ and the sum of $R_A$ and $R_C$ is in the range of from about 0.9:1.1 to about 1.1:0.9.

8. The method of claim 6 wherein the molar ratio of $R_A$ to $R_C$ is in the range of from about 8:92 to 50:50.

9. The method of claim 1 wherein the polyester comprises about one mole of a dicarboxylic acid member and one mole of a diol member wherein said acid member is selected from the group consisting of compounds with two carboxylic acids moieties linked by an aliphatic chain of 1–34 carbon atoms, a cycloaliphatic chain of 3–34 carbon atoms, an arylene chain of from 9–34 carbon atoms, an alkylene chain of from 7–34 carbon atoms, and an alkarylalkylene chain of from 8–34 carbon atoms, or mixtures thereof, and wherein said diol member is comprised of a first dimer diol component having 36 carbon atoms, and a second dihydric alcohol component having the formula C= the group ($-O-R_C-O-$) from a dihydric alcohol wherein $R_C$ is a member selected from the group consisting of compounds of the formula:

$R_C=(CH_nR_m)_k$ where
n= 0, 1, 2, or 3
R= H or a $C_1$ to $C_{10}$ alkyl
m=0, 1, or 2
n+m=2
k=1 to 10.

10. The method of claim 9 wherein said acid member is selected from the group consisting of compounds with two carboxylic acids moieties linked by an aliphatic chain of 3–34 carbon atoms.

11. The method of claim 9 wherein the polyester has a hydroxyl value of less than 25 and an acid value of 2 or less.

12. The method of claim 9 wherein in the polyester the dicarboxylic acid member is adipic acid, and the second dihydric alcohol component is propylene glycol.

13. The method of claim 12 wherein in the polyester the molar ratio of the dicarboxylic acid member to the diol member is in the range from about 0.9:1.1 to about 1.1:0.9.

14. The method of claim 12 wherein in the polyester the molar ratio of the first dimer diol component to the second dihydric alcohol component is in the range of from about 8:92 to about 50:50.

* * * * *